United States Patent [19]

Staats

[11] Patent Number: 5,417,968
[45] Date of Patent: May 23, 1995

[54] ANTIMICROBIAL BARRIER COMPOSITION

[75] Inventor: Victor Staats, Miami Beach, Fla.

[73] Assignee: International Laboratory Technology Corp., Miami Beach, Fla.

[21] Appl. No.: 106,513

[22] Filed: Aug. 16, 1993

[51] Int. Cl.⁶ ............ A61K 31/74; A01N 25/08; A01N 25/34
[52] U.S. Cl. ................... 424/78.07; 424/405; 424/409; 424/411
[58] Field of Search ............ 424/405, 78.07, 409, 424/411

[56] References Cited

U.S. PATENT DOCUMENTS 5,232,691  8/1993  Lemole ..................... 424/78.07

*Primary Examiner*—Thurman K. Page
*Assistant Examiner*—Carlos Azpuru
*Attorney, Agent, or Firm*—Robert M. Downey

[57] ABSTRACT

A moisture activated, antimicrobial barrier composition is provided which can be applied to human skin, especially the hands prior to donning disposable latex gloves. This composition, in a preferred embodiment, contains one or more quaternary ammonium compounds and nonoxynol 9 in a functional complex as the pathogenic growth inhibitor.

8 Claims, No Drawings

ANTIMICROBIAL BARRIER COMPOSITION

BACKGROUND OF THE INVENTION

1. Field of the Invention

The present invention relates to an antimicrobial barrier, and more particularly to a moisture activated antimicrobial composition which can be applied topically to the skin for use in the medical industry.

2. Brief Description of the Prior Art

The prior art has contemplated many methods to afford protection to health care workers and patients against AIDS, hepatitis, and other potentially harmful viruses and bacteria. It is currently standard practice for all workers in the health care industry to wear disposable latex gloves at all times when in contact with patients and invasive medical devices. The gloves, although generally beneficial, can become punctured, torn, or chemically degraded, which potentially puts the wearer at risk of infection, especially if the wearer has sustained a laceration or open wound to the hand or adjacent skin area. Another potential danger of infection exists in the fact that most disposable gloves cover only the fingers, hand, and lower wrist, thus leaving the lower forarm unprotected and open for possible contact with infected fluids and materials. Although it is current procedure for health care workers to wear long sleeved garments, when such a worker engages in any activity requiring extension of their arms, the lower edge of the sleeve will ride up, thereby creating a significant unprotected gap between the garment and glove.

SUMMARY OF THE INVENTION

The present invention provides a novel composition which can be topically applied to the skin, and in particular the hands and lower arms before donning latex gloves, to provide an antimicrobial barrier against a broad spectrum of potential pathogens. In accordance with this invention, the novel composition is moisture activated such that once applied to the skin, it forms a waterproof protective barrier lasting 6 or more hours, which remains inert until it comes into contact with bodily secretions, sweat, water, or other liquid in general. A hydrophilic polymeric component of the composition breaks down and precipitates upon contact with moisture, thus activating the composition. The barrier composition, once activated, continues to afford protection for up to 4 hours. The active antimicrobial component of the composition consists of a mixture of one or more quaternary ammonium compounds and nonoxynol 9.

It is therefore an important object of the present invention to provide a convenient and effective means for protecting patients and medical personnel against infection.

It is a further object of the present invention to provide an antimicrobial barrier composition which can be applied topically to the skin with no adverse dermatological effect.

A further object lies in the provision of an antimicrobial composition which forms a prophylactic barrier upon application to the skin, but upon contact with fluid or moisture, activates to effectively eliminate any pathogens present in the fluid or on the proximate skin surface.

It is yet a further object of the present invention to provide a barrier composition wherein the active antimicrobial component consists of one or more quaternary ammonium compounds and nonoxynol 9.

These and other objects will become readily apparent from the detailed description which follows.

DETAILED DESCRIPTION OF THE PREFERRED EMBODIMENT

The present invention is directed to a moisture activated barrier composition for topical application to human skin. Incorporated into and throughout the composition is a functional substance which is biologically active against a broad spectrum of viruses, bacteria, fungii, and other pathogenic species. A large number of biologically active substances are available which retard bacterial, microbial, or fungal growth. It is contemplated that any of these commonly known biologically active substances could be utilized, however, in the preferred embodiment, the functional substance is comprised of one or more quaternary ammonium compounds and nonoxynol 9. The preferred first quaternary ammonium compound is a blend of Myristalkonium chloride and Quaternium 14 shown by the general formula:

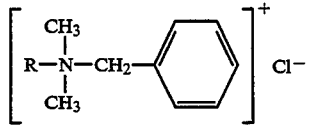

R is 60% C14, 30% C16,
5% C12, 5% C18 n-alkyl dimethyl benzyl
ammonium chloride

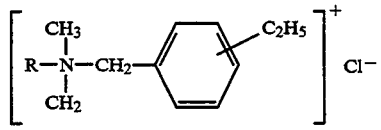

R is 68% C12, 32% C14 n-alkyl dimethyl ethylbenzyl
ammonium chloride

The preferred second quaternary ammonium compound is a mixture of alkylbenzyldimethylammonium chlorides (Benzalkonium Chloride) of the general formula:

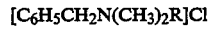

[C$_6$H$_5$CH$_2$N(CH$_3$)$_2$R]Cl wherein R is alkyl

Nonoxynol 9 is an ethoxylated nonyl phenol containing 9 moles of ethylene oxide and serves both as a nonionic surfactant and an antimicrobial agent. Although both nonoxynol 9 and each of the quaternary ammonium compounds can function alone, a synergistic effect is achieved when they are used in combination, producing substantially greater activity against pathogenic species. The nonoxynol 9 enables the composition to be spread evenly over the entire surface of the skim, thus achieving and maintaining a uniform antimicrobial effectiveness throughout. It further acts as a wetting agent which broadens the effectiveness of the quaternary ammonium compounds. Nonoxynol 9 is preferably present in the amount of 2%–5% by weight, the first quaternary ammonium compound blend in the amount of 0.02%–1% by weight, and the benzalkonium chloride in the amount of 0.1%–0.13% by weight.

The barrier composition additionally contains a hydrophobic, waterproofing agent. The hydrophobic agent is preferably a polymer derrived from vinylpyrrolidone and a long chain alpha olefin represented by the general formula:

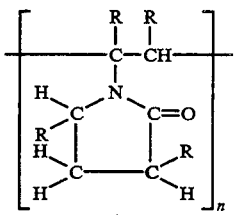

wherein R is alkyl or hydrogen

In the preferred embodiment, the hydrophobic agent is a PVP/eicosene copolymer (polyvinylpyrrolidone and eicosene) and is present 3%–7% by weight.

A hydrophilic film forming compound which is highly moisture sensitive and breaks down upon contact with water is further included in the barrier composition. The film forming compound provides an adhesive type barrier between the functional substance and the environment, thus rendering the composition inert. Upon contact with blood or other bodily secretion, water, or any moisture or fluid in general, the hydrophilic film forming compound breaks down and precipitates, thereby allowing the functional substance to migrate to the outer surface of the skin to effectively eliminate any pathogens present in the fluid or proximate to such. Once the film forming compound breaks down, the functional substance continues to inhibit microbial growth at the surface of the skin for up to 4 or more hours.

Although many hydrophilic film forming agents are contemplated, preferred species include alkyl monoesters of poly(methyl vinyl ether/maleic acid), represented by the following formula:

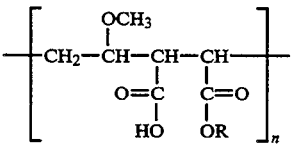

R is ethyl, isopropyl, or n-butyl

Most particularly the ethyl ester of PVM/MA copolymer is selected with a molecular weight between 110,000–150,000 and present from 1%–7% by weight. These compounds are preferred due to their exceedingly high water sensitivity upon neutralization.

Due to the general water insoluability of the hydrophilic film forming compound, the inclusion of 3%–7% by weight of an organic solvent is contemplated with anhydrous ethanol SD 40 being preferred. The organic solvent also functions as a drying agent. Anhydrous ethanol SD 40 and most other commonly utilized organic solvents exhibit relatively high flammability characteristics, therefore requiring that a stabilizer that effectively eliminates the flammable nature of the mixture be included. The use of any of the well known stabilizers of, the prior art is acceptable, however, 2%–5% by weight of 1,3 butylene glycol is a preferred species. 1,3 butylene glycol not only effectively stabilizes the ethanol or other solvent, but further aids in dispersion.

The vehicle for the composition consists of 3%–7% by weight of a resinous hydrophilic water-swellable polymer that provides thickening. Many such resins are ,contemplated in the scope of the present invention. In a preferred embodiment, a cross-linked acrylic acid polymer, such as carbopol 940, manufactured by B. F. Goodrich, is selected. The acrylic acid polymer is in admixture with 3%–7% by weight of an inorganic silicate which is water insoluable. The inorganic silicate, such as Laponite XLG, distributed by Laparte, Inc., provides a support mechanism for the acrylic acid polymer.

The use of a catalyst is further contemplated. The catalyst may be chosen from any of the known catalysts in the polymer industry, although in the present invention, triethanolamine (TEA) is particularly suitable. The triethanolamine, at 1%–3% by weight, increases the hydration, swelling, and thickening efficiency of the acrylic acid polymer.

The formation of the barrier composition includes the use of four separate stainless mixing tanks. In a first mixing tank, ½ of the total volume of the stabilizer (butylene glycol) and the hydrophobic waterproof polymeric compound (PVP/eicosene) are combined and heated to 120 degrees F until the resultant mixture is dissolved and in solution. This mixture is then cooled to room temperature. In a second tank, the balance of the 1,3 butylene glycol is combined with the functional substance (quaternary ammonium compound blend, benzalkonium chloride, and nonoxynol 9). The contents of the first and second tanks are then combined and stirred until homogenous. In a third tank, the cross-linked acrylic acid polymer is combined with deionized water to bring the mixture to the desired concentration. The inorganic silicate is then stirred into the third tank until in solution. The previously combined mixtures from the first and second tanks are then added to the third tank along with the catalyst (triethanolamine). In a fourth tank, the hydrophilic film forming compound (PVM/MA) is then dissolved in the organic solvent (ethanol). The contents of the fourth tank are then introduced very slowly to the third tank, mixing until a homogenous mixture is achieved, and thus forming the novel antimicrobial barrier composition.

It is contemplated that the resultant antimicrobial barrier composition can be topically applied to any external dermal area. All components of the composition are compatible with human skin and adverse or allergic reactions are unlikely. The present invention is particularly directed to the application of the instant composition on the hands and lower forarms prior to donning disposable latex gloves. When initially applied, the composition exists as a physical barrier between the skin and the environment. If a microbe invades the outer dermal surface, the topical composition, in its inert state, prevents the microbe from penetrating further through the layers of skin. However, when the barrier composition encounters fluid or moisture of any type, the functional substance is activated and any pathogens or microbes coexisting on the dermal surface are effectively eliminated for up to 4 hours. When the barrier composition is applied beneath disposable gloves, the composition will generally be activated after a very short time as it is known that human hands will perspire when gloved with latex or other rubber type material.

The barrier composition is further defined by the following examples.

EXAMPLE 1

Agar media and petri culture dishes were prepared. A three member panel was selected.

The hands of Subject #1 were washed with a surgical scrub. The barrier composition was then applied to the entire surface of both hands. Subject #1's hands were then gloved with disposable latex gloves.

Subject #2 followed the same procedure as Subject #1 but the hands were not gloved.

Subject #3 washed with a liquid soap "Dial" and then the barrier composition was applied. The hands of Subject #3 were not gloved.

The hands of all 3 subjects were plated at the end of 2,4,6, and 8 hours. At the end of 4 hours Subject #1 and #2 reapplied the barrier composition. Positive and negative controls were also plated and incorporated into the data.

Results:
Plate Counts at 24 HR Incubation at 35 degrees C.

| Subject | Wt. BG D | 2 HR | 4 HR | Wt. BC G | 6 HR | 8 HR |
|---|---|---|---|---|---|---|
| 1 | 1.10 gm | NG* | NG | 1.15 gm | NG | NG |
| 2 | 0.6 gm | 113+ | 156 | 0.75 gm | 73 | 1841 |
| 3 | 1.2 gm | TNTC^ | TNTC | 0.0 gm | TNTC | TNTC |

Controls
Negative Control - NG after 24 hours incubation.
Positive Control - TNTC after 24 hours incubation.
*NG is equivalent notation for "No Growth"
+Numerical counts denote actual numbers of bacteria colony forming units.
^TNTC is equivalent to bacteria colony forming units that are too numerous to count.

A residual test was also conducted using only Subject #3 from the first panel. The hands of Subject #3 were washed using the surgical scrub. The barrier composition was applied and the hands were not gloved. The hands of Subject #3 were plated after 2,4,6, and 8 hours. There was no reapplication of the composition but the hands were misted with deionized water and allowed to dry before each plating procedure. The same positive and negative controls were utilized.

Residual Test Results:
Plate Counts at 24 HR Incubation at 35 degrees C.

| Subject | Wt. BG D | 2 HR | 4 HR | 6 HR | 8 HR |
|---|---|---|---|---|---|
| 3 | 1.3 gm | 65 | 43 | 41 | TNTC |

Negative control - NG after 24 hours
Positive Control - TNTC after 24 hours

EXAMPLE 2

In vitro inactivation of HIV

HIV Virus stocks were diluted with PBS. 1%,10%, and 100% concentrations of the barrier composition were exposed to the HIV dilutions for one minute and then used to infect MT-2 cells. HIV induced syncytium formation was assessed after 6 days of culture.

Results:

| PERCENTAGE OF COMPOSITION | Conc of N9 | LOG REDUCTION OF COMPOSITION | of N9 |
|---|---|---|---|
| 100% | 0.5 | >3.50 | >3.50 |
| 10% | 0.05 | >3.50 | >3.50 |
| 1% | 0.005 | 1.00 | 0.50 |

EXAMPLE 3

A 5 person test panel was instructed to wash hands using a surgical scrub containing 0.75% available iodine. The hands were rinsed followed by a second Scrub. The hands were then rinsed and dried with paper towels. Each subject then applied 2.5 ml of the barrier composition to both hands. Then the hands were gloved using disposable latex gloves. The gloves were removed after 1,2,4,6, and 8 hours and the sweat/barrier composition mixture was recovered, measured, and used to infect MT-2 cells. Untreated and lubricant (vasoline) treated gloved hands were used as controls. The barrier composition was also mixed with latex gloves alone and recovered after 16 hours. The results are listed in the table below.

| Time (hrs) | Hand | Volume of Sweat/Comp. | Log Virus Titer Reduction of Composition |
|---|---|---|---|
| Experiment #1 | | | |
| 1 hr | L | 0.5 | >3.50 |
| 1 hr | R | 0.3 | >3.50 |
| 2 hr | L | 0.5 | >3.50 |
| 2 hr | R | 0.5 | >3.50 |
| 4 hr | L | 0.6 | >3.50 |
| 4 hr | R | 0.7 | >3.50 |
| 6 hr | L | 0.9 | >3.50 |
| 6 hr | R | 0.8 | >3.50 |
| 8 hr | L | 0.9 | 1.00 |
| 8 hr | R | 1.0 | 0.50 |
| Controls: | | | |
| Composition alone | | | >3.50 |
| Composition + Latex (16 hr) | | | >3.50 |
| Untreated Hands & Glove/Sweat (1 hr) | | | 0.25 (range 0.00–0.50) |
| Vaseline-treated Hands & Glove/Sweat (1 hr) | | | 0.50 (range 0.00–1.00) |
| Experiment #2 | | | |
| 1 hr | L | 0.2 | >3.50 |
| 1 hr | R | 0.3 | >3.50 |
| 2 hr | L | 0.6 | >3.50 |
| 2 hr | R | 0.5 | >3.50 |
| 4 hr | L | 0.5 | >3.50 |
| 4 hr | R | 0.8 | >3.50 |
| 6 hr | L | 0.8 | >3.50 |
| 6 hr | R | 1.2 | >3.50 |
| 8 hr | L | 1.0 | 1.33 |
| 8 hr | R | 1.3 | 0.72 |
| Controls: | | | |
| Composition alone | | | >3.50 |
| composition + Latex (16 hr) | | | >3.50 |
| Untreated Hands & Glove/Sweat (1 hr) | | | 0.25 (range 0.00–0.50) |
| Vaseline-treated Hands & Glove/Sweat (1 hr) | | | 0.50 (range 0.00–1.00) |

While this invention has been shown and described in a preferred embodiment, it is recognized that departures may be made within the spirit and scope of the invention which should not therefore be limited except by the following claims and within the doctrine of equivalents.

What is claimed is:

1. An antimicrobial composition for topical application to skin comprising:
   a biocidally effective amount of a functional substance;
   a resinous, hydrophilic water-swellable polymer including a cross-linked acrylic acid polymer and an inorganic silicate providing a skin compatible polymeric vehicle;
   a hydrophobic waterproof polymeric compound in the form of a copolymer of polyvinylpyrrilodone and eicosene;
   a hydrophilic film forming compound in the form of a copolymer of monoethyl ester of poly (methyl vinyl ether) and maleic acid;
   triethanolamine as a catalyst;
   a stabilizer;
   an organic solvent; and
   deionized water.

2. The composition of claim 1, wherein said functional substance is a complex of an ethoxylated nonyl phenol containing 9 moles of ethylene oxide, a mixture of alkylbenzyldimethylammonium chlorides, and a blend of n-alkyl dimethyl benzyl ammonium chloride and n-alkyl dimethyl ethylbenzyl ammonium chloride.

3. An antimicrobial composition for topical application to skin comprising:
   a quaternary ammonium compound in an amount of between 0.02%–1.0% by weight of said composition;
   an ethoxylated nonyl phenol containing 9 moles of ethylene oxide in an amount of between 2.0%–5.0% by weight of said composition;
   a stabilizer in an amount of between 2.0%–5.0% by weight of said composition;
   a hydrophobic waterproof polymeric compound in the form of a copolymer of polyvinylpyrrilodone and eicosene in an amount of between 3.0%–7.0% by weight of said composition;
   a hydrophilic film forming compound in the form of a copolymer of monoethyl ester of poly (methyl vinyl ether) and maleic acid;
   a skin compatible polymeric vehicle including a mixture of a cross-linked acrylic acid polymer in an amount of between 3.0%–7.0% by weight of said composition and an inorganic silicate in an amount of between 3.0%–7.% by weight of said composition;
   triethanolamine as a catalyst in an amount of between 1.0%–3.0% by weight of said composition;
   an organic solvent in an amount of between 3.0%–7.0% by weight of said composition; and
   deionized water.

4. The composition of claim 3, further including a second quaternary ammonium compound including a mixture of alkylbenzyldimethylammonium chlorides in an amount of between 0.1%–0.13% by weight of said composition.

5. The composition of claim 4, wherein said stabilizer is 1,3 butylene glycol.

6. The composition of claim 4, wherein said organic solvent is anhydrous ethanol.

7. The antimicrobial composition of claim 1 produced by a process comprising the steps of:
   a) heating a first portion of said stabilizer and said hydrophobic waterproof polymeric compound in a first mixing tank to form a first mixture;
   b) cooling said first mixture to room temperature;
   c) mixing a second portion of said stabilizer and said functional substance in a second mixing tank to form a second mixture;
   d) combining said first mixture and said second mixture at a slow stir to form a third mixture;
   e) mixing said deionized water and said skin compatible polymeric vehicle in a third mixing tank to form a fourth mixture;
   f) mixing said hydrophilic film forming polymer and said organic solvent in a fourth mixing tank to form a fifth mixture;
   g) combining said third mixture, said fourth mixture, and said catalyst to form a sixth mixture;
   h) adding said fifth mixture to said sixth mixture, stirring until homogenous.

8. The composition of claim 1, wherein said stabilizer is 1,3 butylene glycol and said organic solvent is anhydrous ethanol SD 40.

* * * * *